United States Patent [19]
Boyd

[11] Patent Number: 5,984,896
[45] Date of Patent: Nov. 16, 1999

[54] FIXATED CATHETER

[75] Inventor: Robert B. Boyd, Muskegon, Mich.

[73] Assignee: OJP #73, Inc., Muskegon, Mich.

[21] Appl. No.: 08/959,469

[22] Filed: Oct. 28, 1997

[51] Int. Cl.[6] .................................................. A61M 5/32
[52] U.S. Cl. ........................................... 604/175; 604/523
[58] Field of Search ..................................... 604/158, 174, 604/175, 264, 280

[56] References Cited

U.S. PATENT DOCUMENTS

| | | |
|---|---|---|
| 3,176,690 | 4/1965 | H'Doubler . |
| 3,399,668 | 9/1968 | Lundgren . |
| 3,638,649 | 2/1972 | Ersek . |
| 4,184,497 | 1/1980 | Kolff et al. . |
| 4,266,999 | 5/1981 | Baier . |
| 4,485,300 | 11/1984 | Holter . |
| 4,955,859 | 9/1990 | Zilber . |
| 5,163,924 | 11/1992 | Beverly . |
| 5,188,619 | 2/1993 | Myers . |
| 5,226,890 | 7/1993 | Ianniruberto et al. . |
| 5,454,795 | 10/1995 | Samson . |
| 5,824,054 | 10/1998 | Khosravi et al. ................ 623/1 |

OTHER PUBLICATIONS

Declaration of Carl P. Lebel Regarding Applicant Activity Not Constituting 35 U.S.C. § 102 Activity.
Declaration of Applicant Regarding Applicant Activity Not Constituting 35 U.S.C. § 102 Activity.

*Primary Examiner*—Corrine McDermott
*Attorney, Agent, or Firm*—Warner Norcross & Judd LLP

[57] ABSTRACT

A fixated catheter including a tube and a fixating portion. The fixating portion includes a fixating strip having a plurality of outwardly protruding barbs. The fixating strip is spirally wound about a portion of the tube. The fixated catheter can be inserted into the body to place the fixated portion adjacent to body tissue so that the barbs engage the body tissue to minimize migration of the fixated catheter during chronic use.

19 Claims, 4 Drawing Sheets

FIXATED CATHETER

BACKGROUND OF THE INVENTION

The present invention relates to catheters, and more particularly to fixated catheters suitable for chronic sampling and delivery of fluids.

Catheters can be used to access specific portions of animal (including human) bodies to sample and deliver fluids. Although some applications need only short-term catheterization, many applications—for example, sampling or delivering fluids during experiments, tests, or therapies—require long-term or "chronic" placement of the catheter within a body. As is recognized by those of skill in the art, the migration of a catheter can ruin chronic experiments or therapies. For example, the study of biological activities or properties of new pharmaceuticals in experimental models often requires chronic sampling of the central nervous system fluid. To collect scientifically valid samples during this type of research, the catheter used to sample the fluids must not migrate or change position so that samples are withdrawn from the same point within the body.

Previous attempts to minimize migration of an indwelling catheter include attaching the catheter with screws and wire to bone. However, this attachment method can cause the catheter to wear out about the fixation point during body movements. Further, this method requires a painful, invasive procedure: the dissection of muscle to expose the bone for catheter attachment.

Other attachment methods, such as fixing the catheter in the subcutaneous tissue with discs and purse string sutures, either permit an undesirable amount of movement of the catheter or only maintain the catheter in place for short periods.

A variety of catheter and other medical devices have been designed for short-term and long-term insertion in a body. For example, U.S. Pat. No. 5,454,795 to Samson entitled "Kink-Free Spiral-Wound Catheter" issued Oct. 3, 1995 discloses a catheter for introduction to the vascular system in angioplasty procedures. A polymeric tube is spirally wound with "ribbons" to control the stiffness of the catheter. However, Samson discloses a catheter that slides smoothly through the vascular system rather than fixate in tissue for chronic use.

U.S. Pat. No. 3,399,668 to Lundgren entitled "Disposable Cholangiography Catheter" issued Sep. 3, 1968 discloses a disposable cholangiographic catheter for use in open abdominal surgery. The catheter has an exterior surface friction portion that cooperates with a tying element to prevent movement of the catheter in the bile duct. The friction portion can include ridges and depressions, a roughened abraded area, an adhesive layer on which fine grains of sand are permanently affixed, a tacky adhesive layer, or an adhesive that dries with a fine granular surface. However, to prevent catheter movement, the Lundgren catheter requires a tying element surrounding the cystic duct in which the catheter is inserted. This catheterization system thus necessitates an invasive and awkward surgical procedure for installation.

U.S. Pat. No. 4,955,859 to Zilber entitled "High-Friction Prosthetic Stent" issued Sep. 11, 1990 discloses a urethral stent for the non-surgical management of bladder outlet obstruction caused by an enlarged prostate. The stent includes either a textured fabric outer layer bonded to the tubular body of the stent or a silicon rubber outer jacket with a roughened outer surface. However, Zilber is directed to managing bladder obstructions, and thus fails to provide a fixating system for chronic access to deliver and sample fluids.

U.S. Pat. No. 4,266,999 to Baier entitled "Catheter For Long-Term Emplacement" issued May 12, 1981 discloses a catheter having a roughened exterior surface suitable for tissue ingrowth to provide adhesion between the skin and the roughened surface. However, the Baier catheter system fails to provide means of preventing migration of the catheter prior to tissue ingrowth.

U.S. Pat. No. 3,638,649 to Ersek entitled "Implantable Prosthetic Pass-Through Device" issued Feb. 1, 1972 discloses a catheter that allows skin tissue to form a permanent seal by using a tube having a roughened portion comprising "a myriad of hairy projections." Again, Ersek fails to provide a means of preventing migration of the device prior to tissue ingrowth.

SUMMARY OF THE INVENTION

The aforementioned problems are overcome in the present invention wherein a catheter includes a fixating portion. More specifically, the catheter includes a tube suitable for insertion into a body to deliver and sample fluids. The tube includes a fixation surface along a portion of the tube's external surface. The fixation surface includes a plurality of externally protruding barbs integral to the tube. The barbs are adapted for engaging body tissue to secure the tube in place.

In a preferred embodiment of the catheter, a first portion of the plurality of barbs points towards the distal end of the catheter and a second portion of the plurality of barbs points towards the proximal end of the catheter.

In another preferred embodiment of the catheter, the fixating portion includes a fixating strip engagingly surrounding a portion of the exterior surface of the tube. The fixating strip includes a plurality of externally protruding barbs adapted for engaging body tissue to secure the tube in place. In one aspect of this embodiment, the fixating strip is spirally wound about the exterior surface of the catheter tube.

A second aspect of the invention is a method of making the catheter. A strip is barbed to form a plurality of externally protruding barbs. The strip is wound around a tube to fix the strip to the tube with the barbs protruding outwardly.

A third aspect of the present invention is a method of delivering and sampling fluids to and from a body, including the following steps: (1) puncturing the body with a needle having an interior passageway, (2) inserting through the interior passageway a catheter having a fixating strip surrounding an exterior portion of a tube, the strip including a plurality of externally protruding barbs adapted for engaging body tissue, and (3) withdrawing the needle from about the catheter so that the barbs engage the body tissue.

The fixated catheter of the present invention provides several advantages. First, the fixated catheter can be used to chronically sample body fluids or deliver therapeutic fluids with minimal migration of the catheter. Second, the fixated catheter provides a relatively large fixation surface area, thereby avoiding single point fixation that can cause catheter kinking or wear-through. Third, the fixated catheter can stay in place for as long as six months without the need to immobilize the site at which the catheter is implanted. Fourth, the fixated catheter can be inserted for chronic use with minimal trauma to the body. The fixated catheter can be installed through use of a catheter needle both to avoid the need to dissect through muscle to affix the catheter to bone and also to minimize or eliminate the need for suturing to maintain the catheter in place.

In particular, the fixated catheter of the present invention is useful for subarachnoid, chronic indwelling catheterization to deliver and extract fluids from the central nervous system. This application of the fixated catheter causes minimal disruption of normal brain physiology and anatomy and can be used in fully ambulatory, conscious animals with intact blood brain barriers. Thus, scientists can obtain clean quantities of cerebrospinal fluid over chronic periods. Analysis of this fluid can generate data on conscious models helpful to further many fields of study, including research on cerebrospinal fluids, the blood brain barrier, and the central nervous system.

These and other objects, advantages, and features of the invention will be more readily understood and appreciated by reference to the detailed description of the preferred embodiment and the drawings.

DETAILED DESCRIPTION OF THE PREFERRED EMBODIMENT

I. Summary

Figures 1, 2, 3, 4, 5:
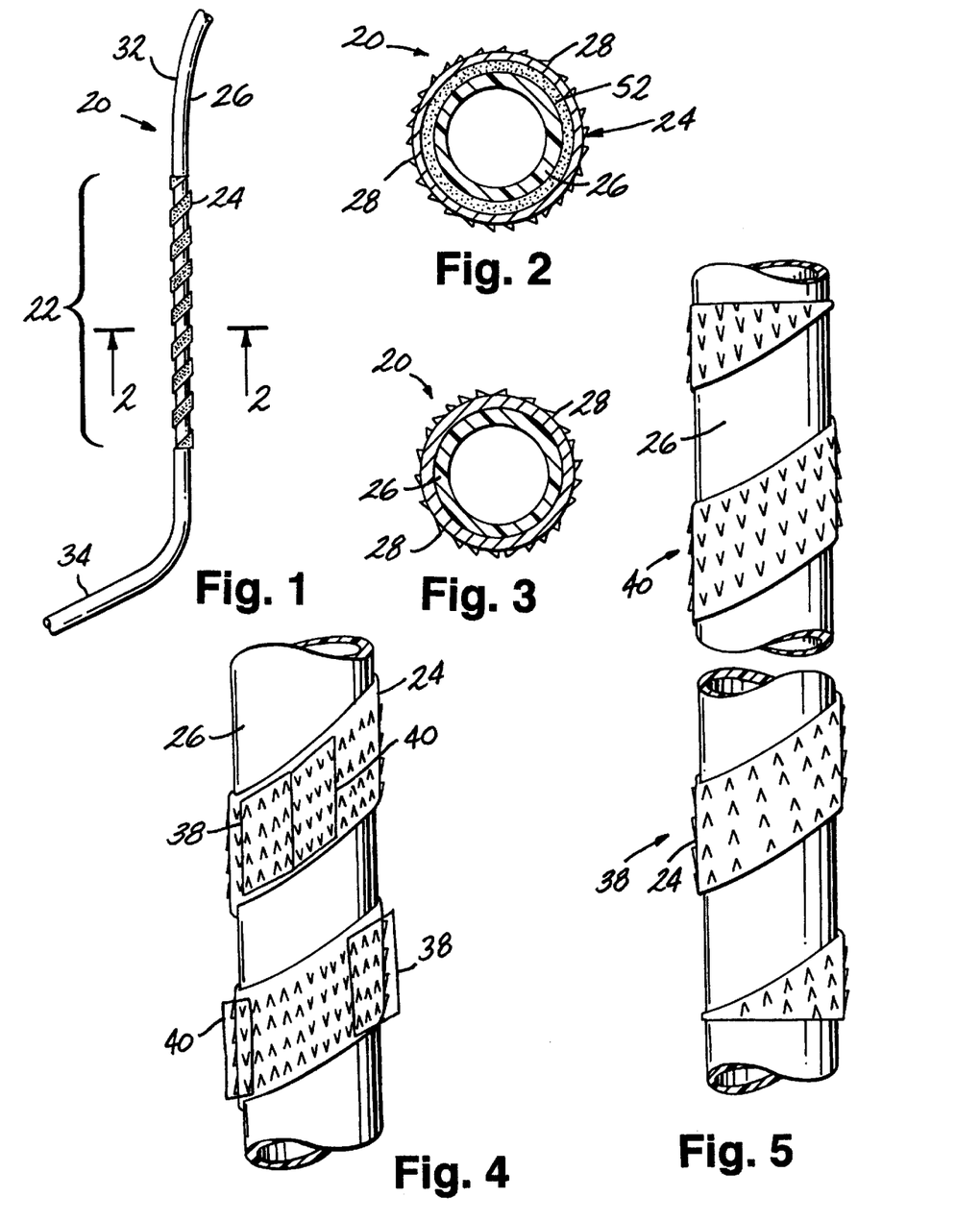
FIG. 1 is a side view of a portion of the fixated catheter of the present invention.
FIG. 2 is an enlarged cross-section view of the fixation catheter taken along line II—II of FIG. 1 showing an embodiment of the present invention including an adhesive layer.
FIG. 3 is an enlarged cross-section view of the fixation catheter taken along line II—II of FIG. 1 showing an alternative embodiment of the present invention without an adhesive layer.
FIG. 4 is a detail view of the fixating portion having the barbs oriented according to one embodiment of the present invention.
FIG. 5 is a fragmentary detail view of the fixating portion having the barbs oriented according to another embodiment of the present invention.
Figures 9, 10:
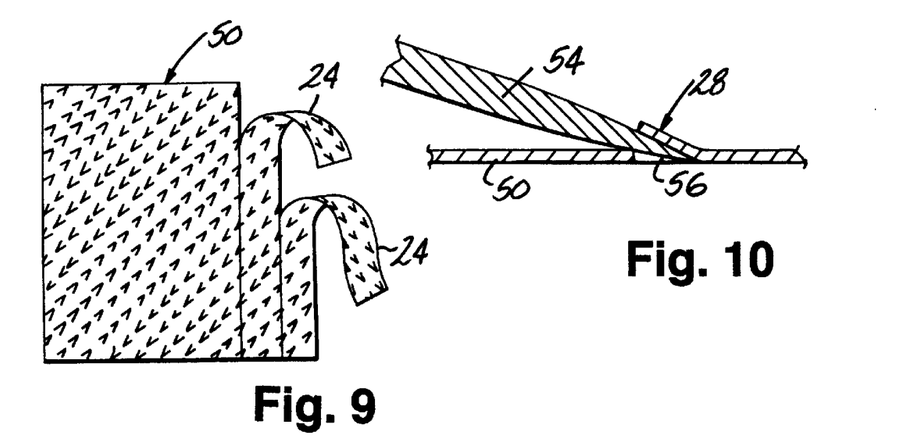
FIG. 9 is a perspective view of a barbed sheet having fixating strips partially removed.
FIG. 10 is a cross-sectional view depicting an alternative manufacturing method including the formation of a barb using a needle.
Figure 11:
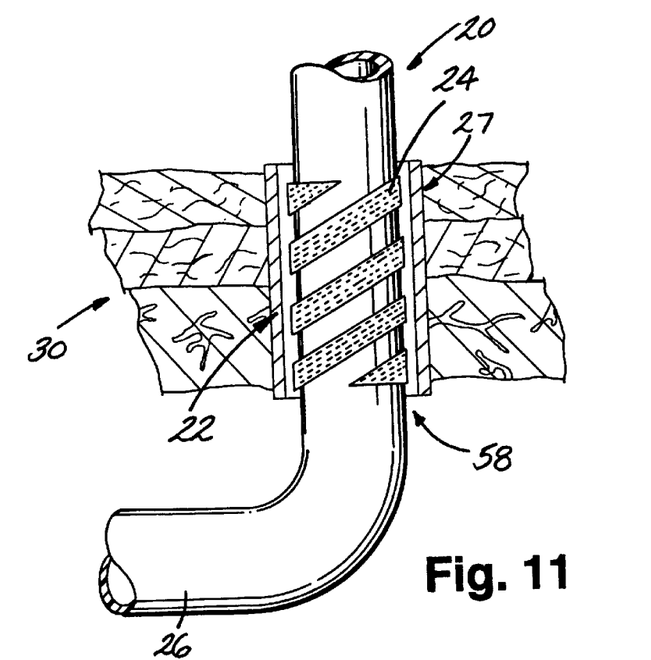
FIG. 11 is a cross-section view of the fixated catheter of the present invention within a catheter needle in turn within body tissue.
Figure 12:
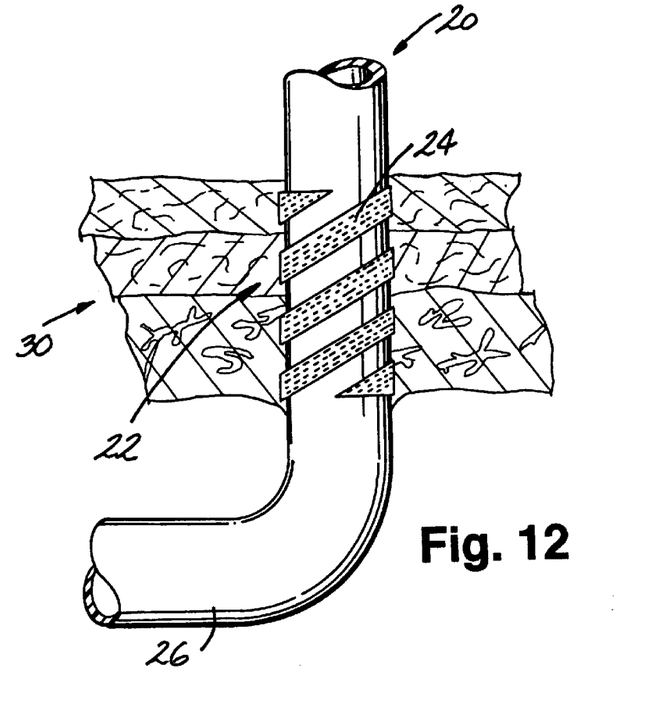
FIG. 12 is a cross-section view of the fixated catheter within bodily tissue.

Referring to the drawings, FIG. 1 shows the fixated catheter 20 of the present invention. The fixated catheter includes tube 26 having a fixating strip 24 spirally wound around it. As shown in FIGS. 2–3, strip 24 includes a plurality of externally protruding barbs 28. These barbs can be formed using a barbing tool 42 (FIG. 6) or by using a needle 54 (FIG. 10). As shown in FIG. 11, the fixated catheter is secured in place by inserting needle 27 through body tissue 30, and then inserting the fixated catheter through needle 28 to place fixating portion 22 adjacent to body tissue 30. As shown in FIG. 12, needle 28 is removed to engage fixating strip 24 with body tissue 30 to secure fixated catheter 20 in place for long term, "chronic" use with minimal migration.

II. Detail of the Structure

A. Tube

Turning to FIG. 1, fixation catheter 20 includes tube 26. Tube 26 has distal end 32 and proximal end 34. Tube 26 is of a type suitable for insertion into a body to deliver and sample fluids. As is well-known in the art, tube 26 can be made from a variety of materials, including polymers such as the polyimides, polyamides (e.g. nylons), polyolefins (e.g., polyethylenes and polypropylenes), polyvinylchlorides, fluoropolymers (e.g., PTFE, FEP, and polyvinylidene fluoride), polysulfones, polyurethanes, and blends, alloys, mixtures, or copolymers thereof. Tube 26 can also be made out of metal or metal alloys, such as stainless steel. The stiffness or flexibility of tube 26 can vary depending on the desired end use as is determinable and well-known by one of skill in the art.

The disclosed tube is intended to sample spinal cord fluids. The tube comprises a flexible plastic having an outer diameter of from about 0.5 to about 3 millimeters, preferably from about 0.7 to about 2 millimeters, and more preferably about 0.9 millimeters, and an inner diameter of from about 0.3 to about 1.8 millimeters, preferably from about 0.4 to about 1.2 millimeters, and more preferably about 0.5 millimeters. A suitable tube for insertion into the cisterna magna of a dog for sampling central nervous system fluid is a 0.9 millimeter outer diameter polyurethane tube having an inner diameter of about 0.5 millimeters.

While the present invention is described in terms of tube 26, it is to be understood that in a broad sense, tube 26 is a medical device designed for insertion into and protrusion from the body. Other medical devices meeting this description include wires, such as chronically implanted electrodes, or other implantable devices, such as fiberoptic fibers or capsules for sustained release of drugs or cells.

B. Fixating Strip

Continuing with FIG. 1, fixated catheter 20 includes fixating portion 22. In one embodiment, fixating portion 22 comprises fixating strip 24 spirally wound about the exterior of tube 26 to engagingly surround it. Fixating strip 24 is preferably made of metal or metal alloy, including aluminum, stainless steel, tungsten alloys, and titanium alloys (e.g., titanium, six percent aluminum, four percent vanadium). The fixating strip 24 can also comprise non-metallic materials, such as plastics, acrylics, or composites, such as carbon composites. For the disclosed application, the fixating strip preferably has a thickness ranging from about 0.001 to 0.005 inches and a width of from about 0.8 to about 0.9 millimeters. For use with a polyurethane tube having 0.9 millimeter outer diameter, aluminum having a thickness of about 0.004 inches is suitable; and a titanium alloy having a thickness of 0.002 inches is suitable.

The term "fixating strip" as used herein also includes a strip in wire form. A fixating strip in wire form is useful for very small applications, for example, when the fixating strip is used with a tube or medical device having a size approaching the lesser values of the above-noted ranges. The fixating strip in wire form has a diameter ranging from about 0.01 to about 0.05 millimeters.

Figure 13:
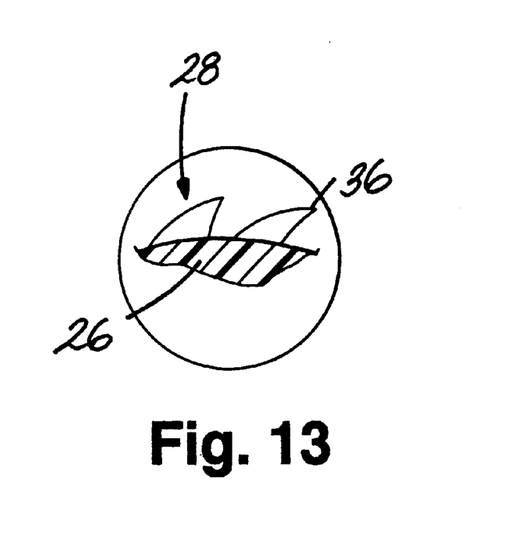
FIG. 13 is an enlarged cross-section view of the barbs of FIG. 3.

As shown in FIGS. 3–5, the fixating strip includes a plurality of externally protruding barbs, quills, burrs, or spines 28. Barbs 28 are adapted for engaging body tissue. As shown in FIG. 13, barb 28 can include point 36. Barbs protruding a distance of from about 2 to about 16 microns have been found suitable for engaging subcutaneous and muscular tissue.

The barb density and orientation, and the length of fixating portion 22, are selected so that the fixating portion can engage body tissue to minimize catheter migration, as discussed below. In the present embodiment, the barbs are spaced to have a density of from about 20 barbs per square inch to about 100 barbs per square inch.

The barbs can be oriented so that points 36 point randomly or in the same alignment. Preferably the barb orientation includes a first portion 38 of barbs 28 pointed toward the distal end 32 of tube 26 and a second portion 40 of barbs 28 pointed toward the proximal end 34 of tube 26. This orientation allows some of the barbs to resist either "pushing" or "pulling" axial forces and thus better resist catheter migration. These first and second barb portions may alternate randomly or systematically. A systematic alternation can more easily assure an equal number of barbs oriented in each direction. One such systematic alternation is shown in FIG. 4, where first portion 38 and second portion 40 circumferentially alternate in longitudinal orientation along the strip.

A most preferred orientation of barbs 28 (FIG. 5) includes first portion 38 of the barbs located toward the proximal end 34 of tube 26 and pointed toward the distal end 32 of tube 26; the second portion 40 of barbs located toward the distal end 32 of tube 26 and pointed toward the proximal end 34 of tube 26. This arrangement better resists catheter migration by requiring the barbs that resist movement in a particular direction to travel a greater length of tissue prior to withdrawal or migration from the tissue.

Fixating portion 22 can extend for a length sufficient to minimize the migration of the fixated catheter. For insertion of the fixated catheter in the cisterna magna of a dog, a fixating portion having a length of about three centimeters in length is suitable. Fixating portion 22 is oriented longitudinally on tube 26 to place fixating portion 22 adjacent to body tissue 30 when proximal end 34 terminates in the desired position within the body. Fixating portion 22 is thus in position to anchor or engage body tissue 30, as described below.

Turning to FIG. 2, in another aspect of the present invention, the fixated catheter can include an adhesive layer 52 to assist in maintaining fixating strip 24 attached to tube 26. The amount and type of adhesive is readily determinable by one of skill in the art.

Figure 14:
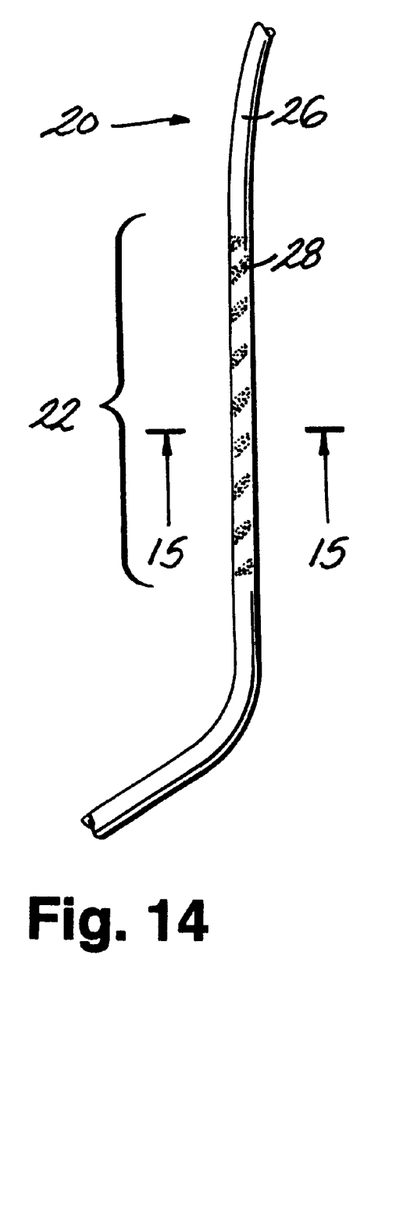
FIG. 14 is a side view of a portion of the fixated catheter having integral barbs according to an alternative embodiment of the present invention.
Figure 15:
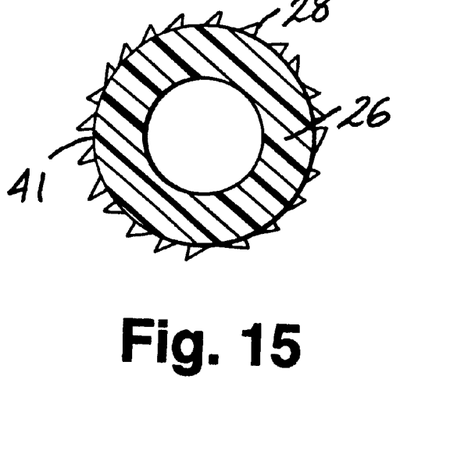
FIG. 15 is an enlarged cross-section view taken along line XV—XV of FIG. 14.

In an alternative embodiment of the present invention, as shown in FIGS. 14—15, tube 26 can include a plurality of externally protruding barbs 28 integral with external surface 41 of tube 26. In this embodiment, the barbs 28 may have any of the orientations or forms as previously discussed.

III. Assembly of the Fixated Catheter

A. Barbing Tool Method

Figures 6, 7, 8:
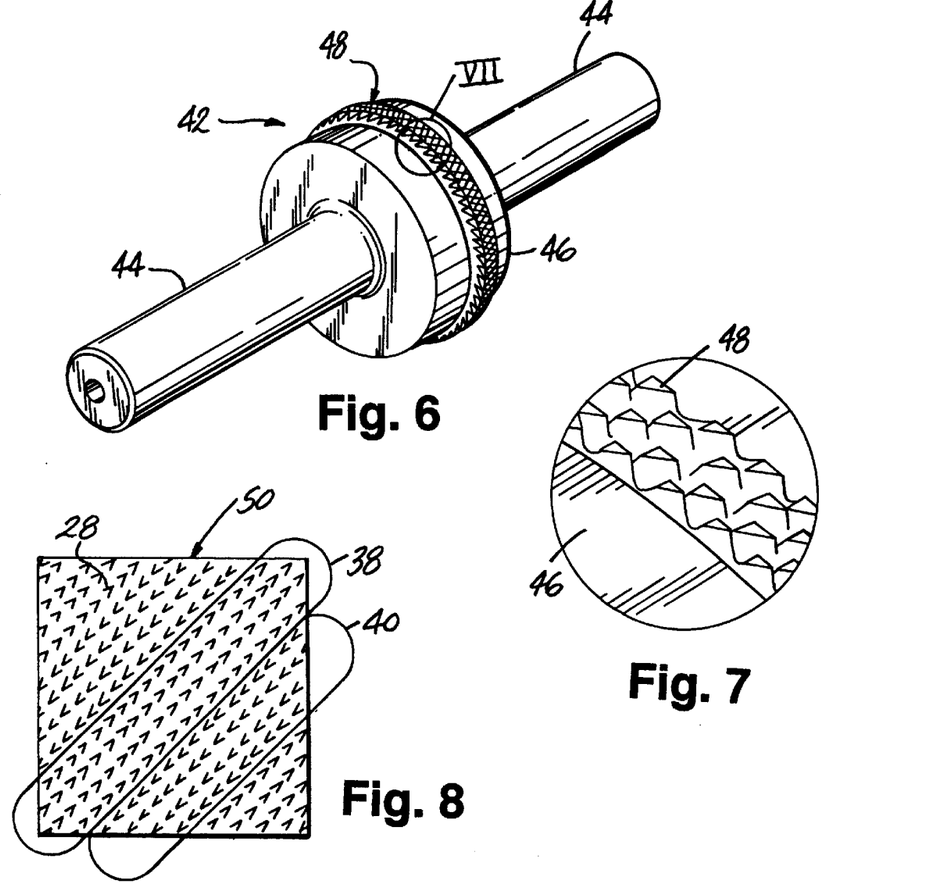
FIG. 6 is a perspective view of the barbing tool used in making the FIG. 4 embodiment.
FIG. 7 is a detailed view of area VII of FIG. 6.
FIG. 8 is a top view of a barbed sheet.

Turning to FIG. 6, barbing tool 42 comprises handles 44 connected to roller 46. Roller 46 includes barbing teeth 48 arranged circumferentially around the central portion of roller 46.

Turning to FIG. 7, barbing teeth 48 extend from the surface of roller 46 from about 0.1 to about 2.5 millimeters. Barbing teeth 48 can assume a variety of configurations depending upon the shape desired for barbs 28. The presently preferred configuration is a plurality of triangularly topped "pyramids."

Barbing tool 42 can be made of any material capable of forming the barbing teeth 48 and having a sufficient weight or strength to indent metal sheet or foil. Suitable materials include metal, wood, and plastic, as is known by one of skill in the art. Barbing tool 42 can be made as one integral piece or comprise an assembly of separate handles 44, roller 46, and barbing teeth 48, as is apparent to one of skill in the art.

The barbing tool 42 is useful to make fixating strips 24 when the strip material comprises a relatively hard metal, such as a titanium alloy. Turning to FIG. 8, barbs 28 can be formed in foil or sheet 50 by rolling barbing tool 42 (FIG. 6) along the surface of sheet 50. Sufficient pressure is applied to barbing tool 42 as it is rolled along the surface of sheet 50 so that barbing teeth 48 indent sheet 50 to form barbs 28. Barbs 28 extend from the surface of sheet 50 on the opposite side of that on which barbing tool 42 is applied. The barbing tool can indent the sheet to form first portion 38 and second portion 40 oriented so that barbs 28 of each portion point in opposite directions. Preferably, the first and second portions of barbs 28 alternate in direction and line up at about a 45° angle orientation relative to the sides of sheet 50.

Turning to FIG. 9, fixating strips 24 can be cut from sheet 50 so that first and second barb portions 38 and 40 maintain a 45° orientation relative to the edges of strip 24. Thus, as fixating strip 24 is spirally wound around tube 26, the barbs will point in longitudinal directions relative to tube 26, as shown in FIG. 4.

The fixation strip can be spirally wound by machine- or hand-rolling the fixation strip 24 and tube 26 together. Once wrapped, the fixating strip 24 is twisted about tube 26 so that the spiral "grabs" the catheter to maintain the fixating strip 24 in position. Thus, the fixating strip engagingly surrounds a portion of the exterior surface of tube 26. The relative stiffness of the fixation strip once twisted also maintains the "free" ends of the strip in position.

B. Adhesive Option

In one aspect of the present invention, adhesive layer 52 is included between fixation strip 24 and tube 26, as shown in FIG. 2. Adhesive layer 52 can assist in holding fixating strip 24 in place while it is spirally wound about tube 26 during assembly of fixated catheter 20. This adhesive "assistance" is helpful in spirally winding strips comprising foils having relatively low stiffness, such as aluminum foils. Adhesive layer 52 can also assist in maintaining fixation strip 24 attached to tube 26 during operation. Adhesive layer 52 can comprise a suitable adhesive as is known by one of skill in the art.

C. Formation of Barbs by Needle Method

FIG. 10 depicts an alternative method of forming barbs 28. Needle 54 is placed in approximately a 30° angle relative to the surface of sheet 50. Tip 56 of needle 54 is inserted into sheet 50. Needle 54 is then uplifted to form an angle of about 50° relative to the sheet, to pull a portion of sheet 50 upward and form barb 28. As barb 28 is formed, a distinct "click" is heard when using a sheet made of aluminum. Needle 54 is of a size suitable to form barbs adapted for engaging body tissue, for example, a 25 gauge needle.

Alternatively, a fixating strip can be spirally wound about tube 26 prior to the formation of barbs 28. After the unbarbed fixating strip is in place about tube 26, needle 54 is used to form barbs 28 as previously described. With this alternative, it is of course important in order to avoid undesirably perforating tube 26 that tip 56 not extend through fixating strip 24 to engage tube 26.

The needle method of forming barbs 28 is advantageously used when fixating strip 24 is made of relatively "soft" materials (e.g., aluminum) when compared to titanium alloy.

D. Integral Barbs

In an alternative embodiment of the present invention in which a plurality of externally protruding barbs 28 are integral to tube 26 along fixating portion 22 (FIGS. 14–15), barbs 28 can be integrally formed in external surface 41 of tube 26. Barbs 28 can be formed or molded in tube 26 during the manufacture of tube 26 or during subsequent processing of tube 26, as is apparent to one of skill in the art.

IV. Operation of the Fixated Catheter

FIGS. 11–12 illustrate the use of fixated catheter 20. A catheter needle or touhy needle 27 is inserted through body tissue 30 to a desired depth, for example, through the dura and into the subarachnoid space. Fixated catheter 20 is inserted through needle 27 until the proximal end 34 of fixation catheter 20 is in the desired position within the body and fixating portion 22 is adjacent to body tissue 30. Catheter needle 27 is of a size sufficient to allow fixation catheter 20 to pass through its interior passageway 58.

The catheter needle 27 is withdrawn so that fixating strip 24 engages body tissue 30 (FIG. 12). Optionally, a purse string suture (not shown) can be used to tighten the skin at the entry point about the catheter. Once implanted, barbs 28 engage in musculature and other tissue of body tissue 30 to fixate or hold the catheter in place until fibroblast ingrowth can occur. It is believed that the barbs engage body tissue in a similar manner as a porcupine quill or a fish hook barb. After about 11 days the fibroblast have grown around barbs 28 to assist in preventing catheter migration.

If fixating strip 24 is spirally wound about tube 26, the fixating strip can also constrict about tube 26 to restrict its axial movement when a force is exerted to pull the tube outwardly from the body. Further, the spirally wound fixating strip 24 can also restrict axial movement of tube 26 if the muscular tissue of body tissue 30 tightens about the spirally wound strip 24. In this function, the spirally wound fixating strip 24 is similar to a "Chinese finger trap" toy, which constricts the movement of a child's fingers as the child attempts to pull the finger out of the toy. The "fixation" of the fixation strip is static in the barbs—which hold the tissue—yet the fixation strip tightens on the tube during muscular or dynamic movement.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents.

The embodiments of the invention in which an exclusive property or privilege is claimed are defined as follows:

1. An device comprising:
    a medical device adapted for insertion in a body, said medical device having an exterior surface;
    a strip engagingly surrounding a portion of said exterior surface of said medical device, said strip including a plurality of externally protruding barbs adapted for engaging body tissue to chronically secure said medical device in place, wherein said strip is spirally wound around a portion of said exterior surface of said medical device.

2. A device comprising:
    a medical device adapted for insertion in a body, said medical device having an exterior surface;
    a strip engagingly surrounding a portion of said exterior surface of said medical device, said strip including a plurality of externally protruding barbs adapted for engaging body tissue to chronically secure said medical device in place, wherein said strip constricts about said medical device to reduce the axial movement of said medical device when a force is exerted to pull said medical device outwardly from the body.

3. A device comprising:
    a medical device adapted for insertion in a body, said medical device having an exterior surface, a distal end, and a proximal end opposite said distal end;
    a strip engagingly surrounding a portion of said exterior surface of said medical device, said strip having a distal end proximate said distal end of said medical device and a proximal end proximate said proximal end of said medical device, said strip including a plurality of externally protruding barbs adapted for engaging body tissue to chronically secure said medical device in place;
    each of said barbs comprises a protruding projection having a point;
    a first portion of said barbs points toward said distal end of said strip; and
    a second portion of said barbs points toward said proximal end of said strip.

4. The fixation device of claim 3 wherein:
    said first portion said barbs is located toward said proximal end of said medical device; and
    said second portion of said barbs is located toward said distal end of said medical device.

5. The device of claim 3 wherein a plurality of barbs in said first portion of said barbs substantially alternates along said strip with a plurality of barbs in said second portion of said barbs.

6. A fixation device useful for maintaining the installation in the body of a medical device that has an exterior surface, the fixation device comprising:
    a strip adapted to engagingly surround a portion of the exterior surface of the medical device, said strip including a plurality of externally protruding barbs adapted to engage body tissue to chronically secure the medical device in place, wherein said strip is adapted to spirally wind around a portion of the exterior surface of the medical device.

7. A fixation device useful for maintaining the installation in the body of a medical device that has an exterior surface, the fixation device comprising:
    a strip adapted to engagingly surround a portion of the exterior surface of the medical device, said strip including a plurality of externally protruding barbs adapted to engage body tissue to chronically secure the medical device in place, wherein said strip is adapted to constrict about the medical device to reduce the axial movement of the medical device when a force is exerted to pull the medical device outwardly from the body.

8. A fixation device useful for maintaining the installation in the body of a medical device that has an exterior surface, the fixation device comprising:
    a strip adapted to engagingly surround a portion of the exterior surface of the medical device, said strip including a plurality of externally protruding barbs adapted to engage body tissue to chronically secure the medical device in place, wherein:
    said strip includes a distal end and a proximal end opposite the distal end;
    each of said barbs comprises a protruding projection having a point;
    a first portion of said barbs points toward the distal end of said strip; and a second portion of said barbs points toward the proximal end of said strip.

9. The fixation device of claim 8 wherein:

said first portion of said barbs is located toward the proximal end of said strip; and said second portion of said barbs is located toward the distal end of said strip.

10. The fixation device of claim 8 wherein a plurality of barbs in said first portion of said barbs substantially alternates along said strip with a plurality of barbs in said second portion of said barbs.

11. A catheter comprising:

a tube suitable for insertion into a body to deliver and sample fluids, said tube having an exterior surface; and a strip spirally wound around the exterior surface of said tube to engagingly surround a portion of the exterior surface of said tube, said strip including a plurality of externally protruding barbs adapted for engaging body tissue to secure said tube in place.

12. A catheter comprising:

a tube suitable for insertion into a body to deliver and sample fluids, said tube having an exterior surface; and a strip engagingly surrounding a portion of the exterior surface of said tube, said strip including a plurality of externally protruding barbs adapted for engaging body tissue to secure said tube in place, said strip constricting about said tube to reduce the axial movement of said tube when a force is exerted to pull said tube outwardly from the body.

13. A catheter comprising:

a tube suitable for insertion into a body to deliver and sample fluids, said tube having an exterior surface, a distal end, and a proximal end opposite said distal end; and a strip engagingly surrounding a portion of the exterior surface of said tube, said strip including a plurality of externally protruding barbs adapted for engaging body tissue to secure said tube in place, each of said barbs including a protruding projection having a point; and wherein:

a first portion of said barbs points toward the distal end of said tube; and a second portion of said barbs points toward the proximal end of said tube.

14. The catheter of claim 13 wherein:

said first portion of said barbs is located toward the proximal end of said tube; and said second portion of said barbs is located toward the distal end of said tube.

15. The catheter of claim 13 wherein a plurality of barbs in said first portion of said barbs circumferentially alternates in longitudinal orientation along said strip with a plurality of barbs in said second portion of said barbs.

16. A catheter comprising:

a tube suitable for insertion into a body to deliver or sample fluids, said tube having an exterior surface; and a strip spirally wound around the exterior of said tube to engagingly surround a portion of the exterior surface of said tube, said strip including a plurality of externally protruding barbs adapted for engaging body tissue to secure said tube in place, a majority of said barbs having a point oriented toward an end of said tube.

17. A catheter comprising:

a tube suitable for insertion into a body to deliver and sample fluids, said tube having an external surface, a distal end, and a proximal end opposite said distal end, said external surface including a fixation surface along a portion of said external surface, said fixation surface including a plurality of externally protruding barbs integral to said tubing and adapted for engaging body tissue to secure said tube in place, each of said barbs including a protruding projection having a point; and wherein:

a first portion of said barbs points toward the distal end of said tube; and a second portion of said barbs points toward the proximal end of said tube.

18. The catheter of claim 17 wherein:

said first portion of said barbs is located toward the proximal end of said tube; and said second portion of said barbs is located toward the distal end of said tube.

19. The catheter of claim 17 wherein a plurality of barbs in said first portion of said barbs circumferentially alternates longitudinally along said fixation surface with a plurality of barbs in said second portion of said barbs.

* * * * *

UNITED STATES PATENT AND TRADEMARK OFFICE
CERTIFICATE OF CORRECTION

PATENT NO. : 5,984,896
DATED : November 16, 1999
INVENTOR(S) : Robert B. Boyd

It is certified that error appears in the above-indentified patent and that said Letters Patent is hereby corrected as shown below:

Column 7, Claim 1, Line 50:
"An" should be --A--

Column 8, Claim 4, Line 22:
delete "fixation"

Column 8, Claim 4, Line 23:
after "portion" insert --of--

Signed and Sealed this

Twenty-seventh Day of June, 2000

Attest:

Q. TODD DICKINSON

*Attesting Officer*     *Director of Patents and Trademarks*